(12) United States Patent
Hartwick et al.

(10) Patent No.: US 8,590,764 B2
(45) Date of Patent: Nov. 26, 2013

(54) CIRCUMFERENTIAL FULL THICKNESS RESECTIONING DEVICE

(75) Inventors: Darrell Hartwick, Newton, MA (US); Malka Berndt, Lexington, MA (US); George Nunez, Miami, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1846 days.

(21) Appl. No.: 10/746,549

(22) Filed: Dec. 24, 2003

(65) Prior Publication Data
US 2005/0145675 A1    Jul. 7, 2005

(51) Int. Cl.
*A61B 17/04*    (2006.01)

(52) U.S. Cl.
USPC ............ 227/180.1; 227/179.1; 606/139; 606/153

(58) Field of Classification Search
USPC .......... 606/139, 153; 227/176.1, 179.1, 180.1
See application file for complete search history.

(56) References Cited

U.S. PATENT DOCUMENTS

| | | | |
|---|---|---|---|
| 3,193,165 A * | 7/1965 | Burtsev et al. ................. 227/8 |
| 4,198,982 A * | 4/1980 | Fortner et al. ............. 227/179.1 |
| 4,207,898 A * | 6/1980 | Becht ........................ 227/179.1 |
| 4,304,236 A * | 12/1981 | Conta et al. ............... 227/179.1 |
| 4,573,468 A * | 3/1986 | Conta et al. ............... 227/179.1 |
| 4,576,167 A * | 3/1986 | Noiles ....................... 227/179.1 |
| 4,603,693 A * | 8/1986 | Conta et al. ............... 227/179.1 |
| 4,646,745 A * | 3/1987 | Noiles ....................... 227/178.1 |
| 5,205,459 A * | 4/1993 | Brinkerhoff et al. ...... 227/179.1 |
| 5,411,508 A * | 5/1995 | Bessler et al. ............... 606/153 |
| 5,588,579 A * | 12/1996 | Schnut et al. ............. 227/175.1 |
| 5,669,918 A * | 9/1997 | Balazs et al. ................ 606/139 |
| 5,839,639 A * | 11/1998 | Sauer et al. ............... 227/175.1 |
| 5,868,760 A * | 2/1999 | McGuckin, Jr. ............. 606/139 |
| 6,004,335 A * | 12/1999 | Vaitekunas et al. .......... 606/169 |
| 6,050,472 A * | 4/2000 | Shibata ..................... 227/175.2 |
| 6,126,058 A * | 10/2000 | Adams et al. ............. 227/180.1 |
| 6,179,195 B1 * | 1/2001 | Adams et al. ............. 227/180.1 |
| 6,264,086 B1 * | 7/2001 | McGuckin, Jr. .......... 227/180.1 |
| 6,302,311 B1 | 10/2001 | Adams et al. |
| 6,343,731 B1 * | 2/2002 | Adams et al. ............. 227/180.1 |
| 6,585,144 B2 * | 7/2003 | Adams et al. ............. 227/175.1 |

\* cited by examiner

*Primary Examiner* — Darwin Erezo
(74) *Attorney, Agent, or Firm* — Fay Kaplun & Marcin, LLP

(57) ABSTRACT

An apparatus for performing endoluminal anastomosis of an organ comprises an operative head including an endoscope receiving lumen for slidably receiving a flexible endoscope therein, the operative head including an annular tissue receiving space extending around a circumference of a distal end thereof and a stapling mechanism for firing staples around an entire circumference of the tissue receiving space and a tissue gripping mechanism for drawing into the tissue receiving space a portion of tissue extending around an entire circumference of the organ.

14 Claims, 9 Drawing Sheets

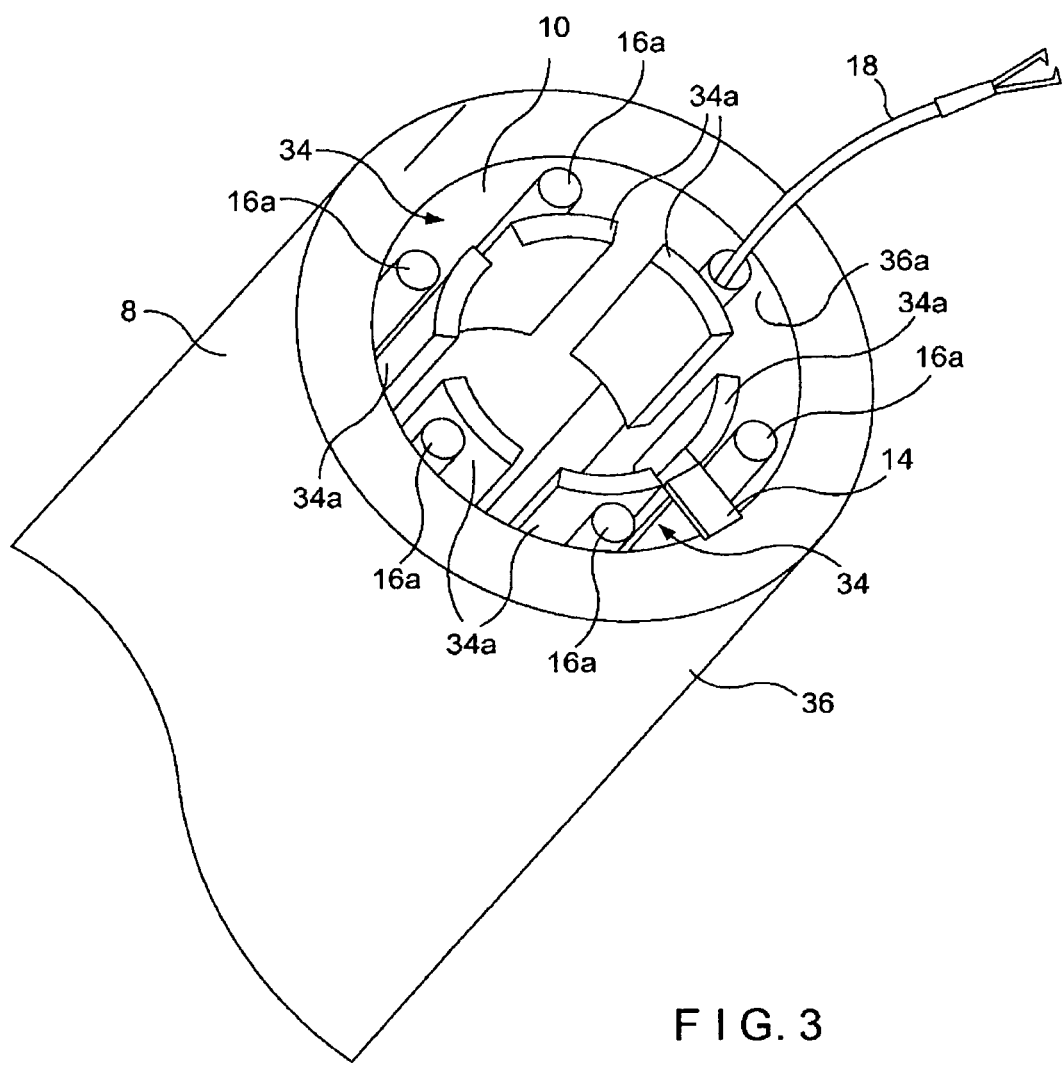
F I G. 3

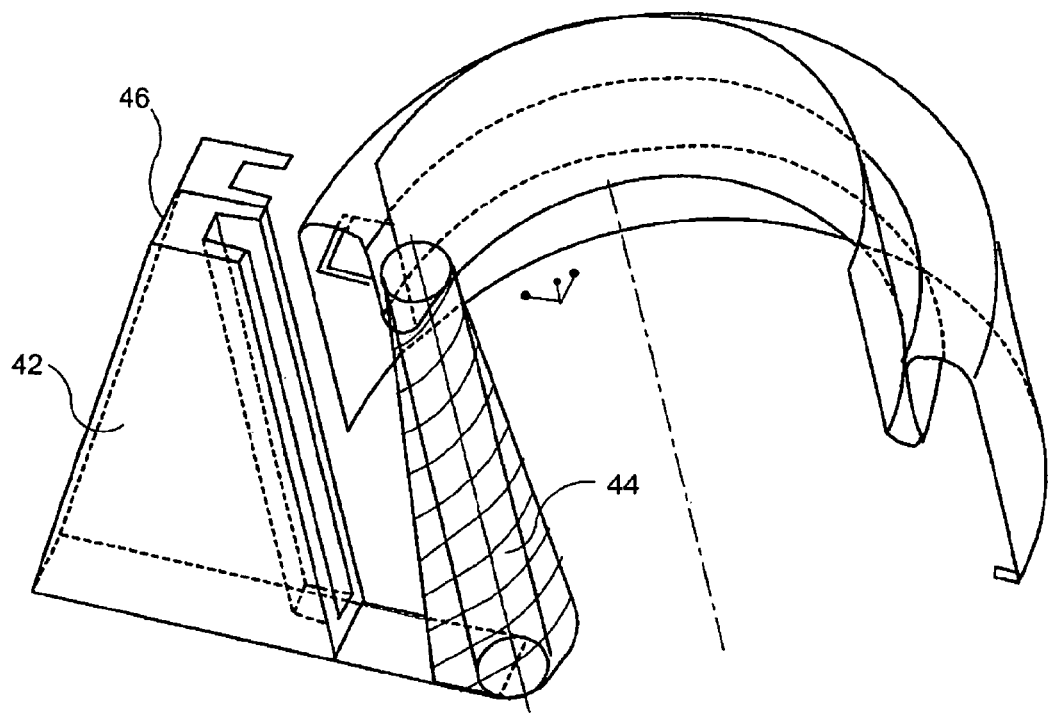
F I G. 6
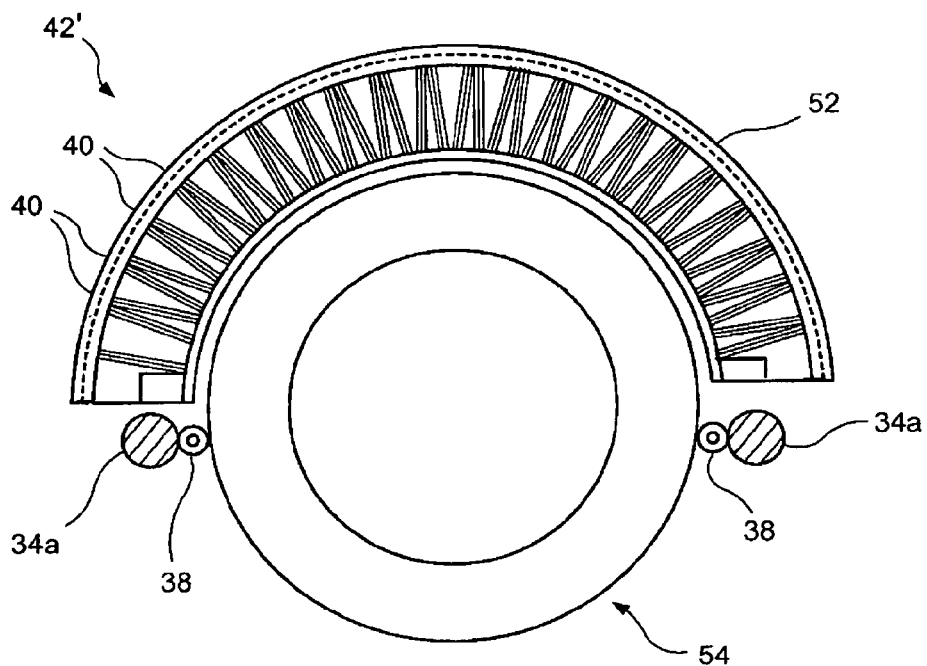
F I G. 7

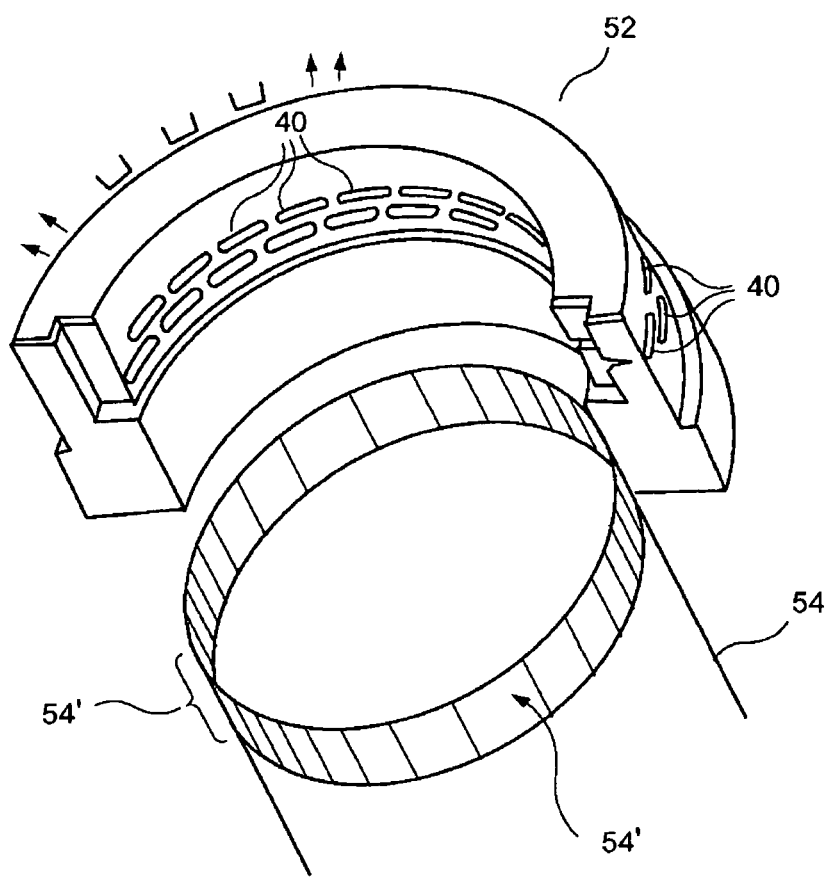
F I G. 8

CIRCUMFERENTIAL FULL THICKNESS RESECTIONING DEVICE

FIELD OF THE INVENTION

The present invention relates to full thickness resection devices for performing localized resections of lesions and devices for performing circumferential anastomoses.

BACKGROUND OF THE INVENTION

Resectioning procedures involve excising a portion of an organ, stapling the surrounding sections together to close up the hole created by the excision, and removing the excess tissue resulting from the stapling. Various conventional devices are available for resectioning lesions in tubular organs.

Several known resectioning devices require at least one incision in an area near the portion of the organ to be excised because, for example, the resectioning device may lack steering and/or viewing capabilities. Specifically, devices for performing circular anastomoses of substantially tubular organs have been used in conjunction with open surgery. For example, devices are known for use in joining sections of the colon which have been separated from one another by the surgical removal of a cylindrical section of the colon. The separated ends are first purse stringed to seal the interior of the colon and a part of the device (e.g., the anvil of a stapling apparatus) is placed within one of the purse stringed ends while the rest of the device is advanced through the colon to the other purse stringed end (usually via an additional incision). The two purse stringed ends are then brought together and the anvil is joined to the rest of the device. A circular line of staples joins the two sections of the colon and the tissue radially within this line of staples is cut away and removed to open the lumen of the rejoined colon. Of course, these incisions are painful and may involve a partial or entire loss of mobility while recuperating from the incision, in addition to the pain and inconvenience associated with recovery from the resectioning procedure itself. Furthermore, the time required to recover from such a procedure is often longer than for procedures which do not require incisions.

SUMMARY OF THE INVENTION

The present invention is directed to an apparatus for performing endoluminal anastomosis of an organ, comprising an operative head including an endoscope receiving lumen for slidably receiving a flexible endoscope therein, the operative head including an annular tissue receiving space extending around a circumference of a distal end thereof and a stapling mechanism for firing staples around an entire circumference of the tissue receiving space and a tissue gripping mechanism for drawing into the tissue receiving space a portion of tissue extending around an entire circumference of the organ.

BRIEF DESCRIPTION OF THE DRAWINGS

FIG. 3 shows a perspective view of a distal end of a working head assembly of the device of FIG. 1 with the distal cap not shown;
FIG. 6 shows a partially cross-sectional view of the anvil and stapling mechanism of FIG. 5;
FIG. 7 shows a partially cross-sectional view of an alternate stapling mechanism for use with an apparatus according to the invention in a plane substantially perpendicular to a longitudinal axis of the device;
FIG. 8 shows a partially cross-sectional perspective view of the stapling mechanism of FIG. 7.

DETAILED DESCRIPTION

Figure 1:
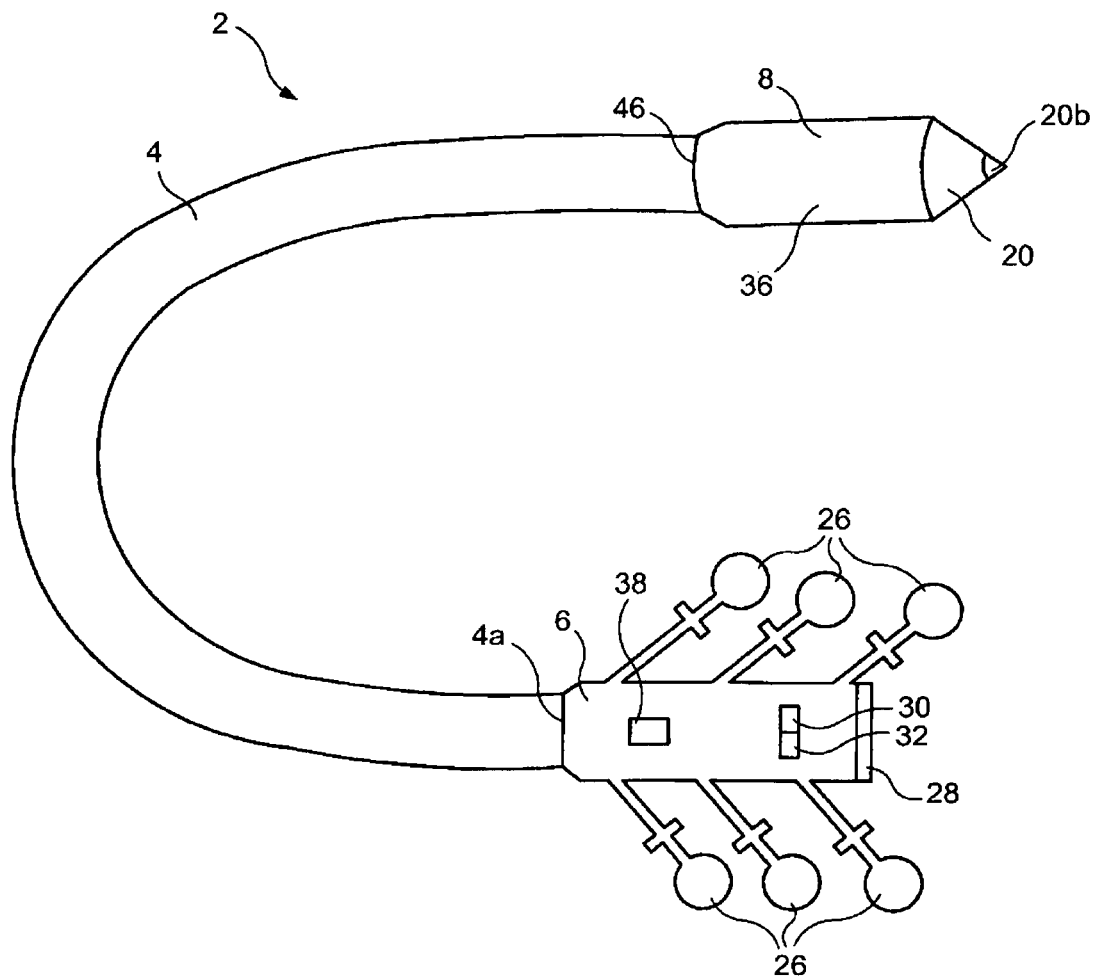
FIG. 1 shows a perspective view of a device according to a first embodiment of the present invention with a distal cap of the device closed.

A detailed description of illustrative embodiments of the present invention is provided in conjunction with the attached drawings. In the descriptions of the various embodiments and the corresponding drawings, like reference numerals refer to like elements.

A device 2 according to a first embodiment of the invention is shown in FIGS. 1-5. The device 2 includes a flexible sheath 4 extending from a proximal end 4a which is coupled to a control handle 6 to a distal end 4b which is coupled to a working head assembly 8. The working head assembly 8 includes an annular tissue receiving space 10 adjacent to a stapling apparatus 12, a tissue cutting mechanism 14 and a plurality of lumens 16 through which tissue grasping devices 18 may be deployed. As will be described in more detail below, the working head assembly 8 also includes a distal cover 20 which is moveable between a closed position for insertion and retraction of the device 2 from the body and an open position in which the tissue receiving space 10, the stapling apparatus 12 and distal openings 16a to the lumens 16 are exposed to the interior of the organ. Those skilled in the art will understand that, although this illustrative embodiment shows six (6) such lumens 16, more or fewer of these lumens 16 may be employed (with or without a corresponding change in the number of grasping devices 18) depending on the size of the organ and the characteristics of the grasping devices 18 to be employed. The device 2 also includes an endoscope receiving lumen 22 extending through the control handle 6, into the sheath 4 and through the working head assembly 8. In use, as will be more fully described below, a steerable endoscope 24 (as are known in the art) may be slidably received therein.

Those skilled in the art will understand that the sheath 4 provides a flexible, torque carrying connection between the control handle 6 and the working head assembly 8, creating a channel therebetween to support the drive mechanisms for the working head 8, the endoscope 24, etc. The sheath may preferably be formed as a braid of, for example, stainless steel, MP35N or other material suitable for fine wires or an elastomeric material with a polymer coating, e.g., urethane, silicone or nylon.

Figure 2:
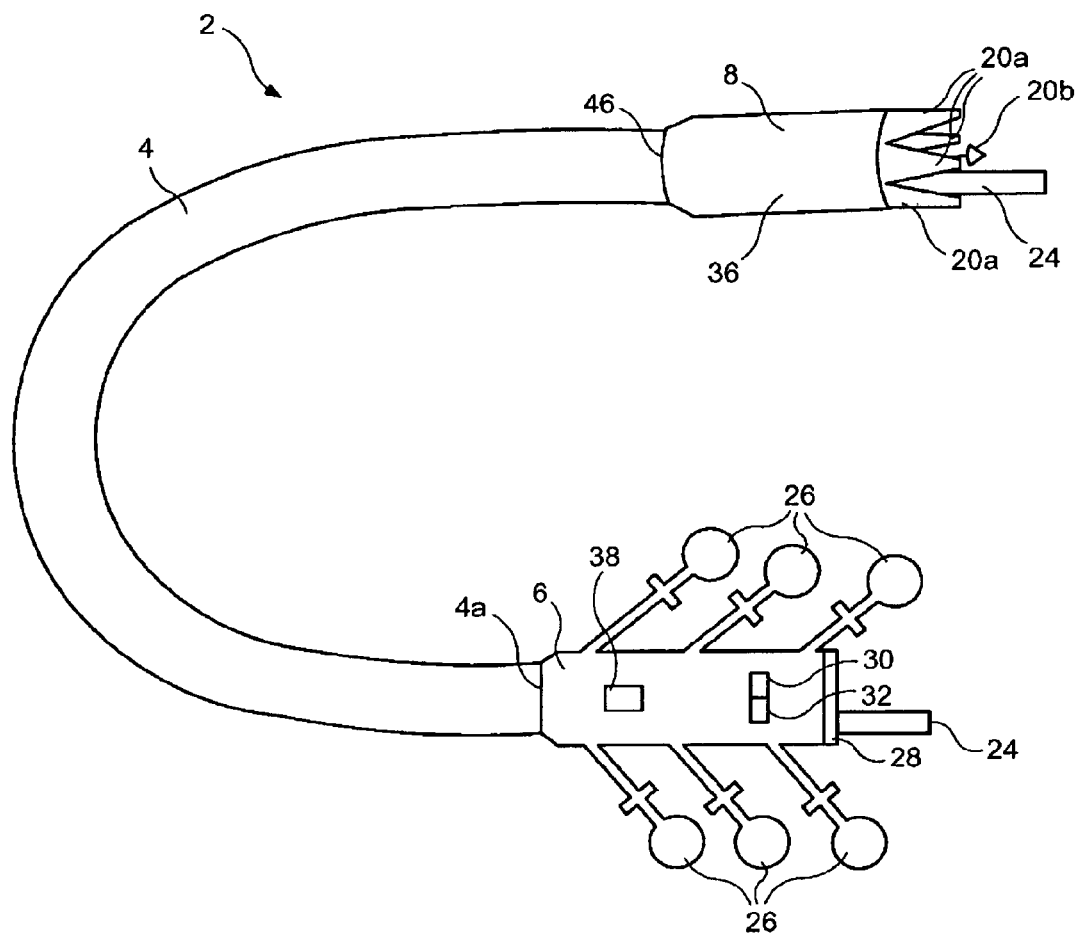
FIG. 2 shows a perspective view of the device of FIG. 1 received on an endoscope with the distal cap open before doors thereof have been drawn into the working head assembly.
Figure 4:
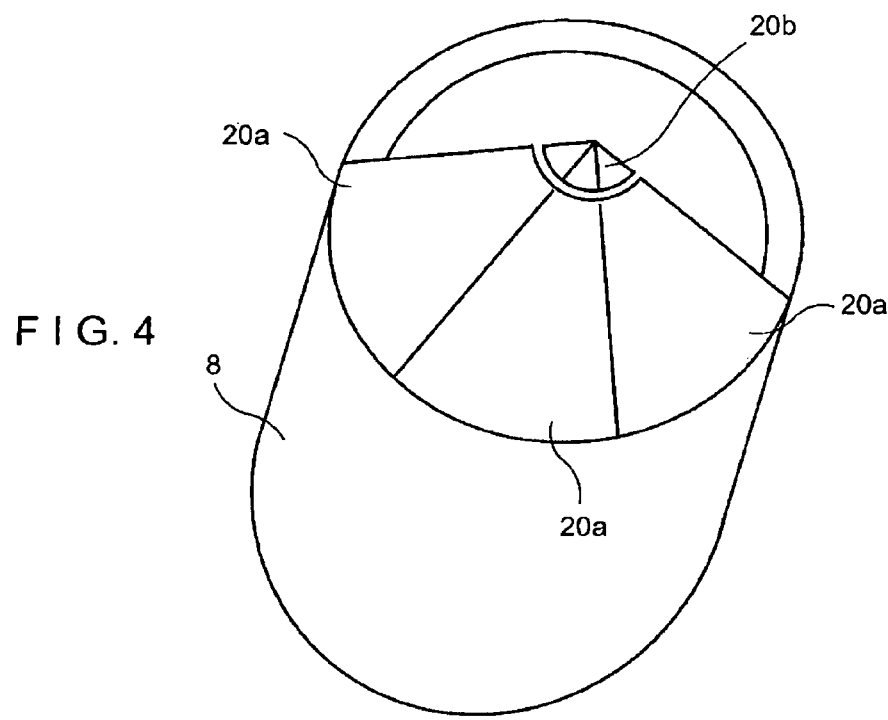
FIG. 4 shows a perspective view of the distal end of the working head assembly of FIG. 3 with a portion of the distal cap in place in the closed position.

As shown in FIGS. 1, 2 and 4, the distal cap 20 includes a plurality of doors 20a moveable with respect to one another from a closed position in which the doors 20a contact one another as well as a central plug 20b to form a substantially conical distal tip of the device 2. Those skilled in the art will understand that, in order to ease insertion of the device 2 into the body and to minimize trauma thereto, the distal ends of each of the doors 20a and/or the central plug 20b may be rounded to form a substantially smooth, rounded distal tip when in the closed position. As would be understood by those of skill in the art, the doors 20a are coupled to one another and to the central plug 20b so that they move between the open and closed positions in synchronization with one another.

For example, in this embodiment, a cover actuator 30 is connected to a pull wire 31 which extends through the sheath 4, into the working head assembly 8 to a rod 33 which is coupled to the central plug 20b. When the actuator 30 is moved toward an open position, the pull wire 31 and the rod 33 draw the central plug 20b proximally into the working head assembly 8 and all of the doors 20a move away from one another to the open position. As the doors 20a are moved to the open position, they may also be drawn proximally along an outer surface of the working head assembly 8. Alternatively, the doors 20a may be moved proximally into an annular lumen (not shown) until distal ends of the doors 20a are received therein.

The actuator 30 may further include a locking mechanism (not shown) for maintaining the cover 20 in the open position, as would be understood by those of skill in the art. Upon release of the locking mechanism, the cover 20 would be returned to the closed position by, for example, a spring biased to draw the doors 20a toward one another. Alternatively, a second pull wire (not shown) may be included which operates, when the actuator 30 is operated in a closing direction, to draw the doors 20a and the central plug 20b into the closed position.

The control handle 6 which remains outside the body during use of the device 2 includes a plurality of grasping device insertion tubes 26 each of which extends to a corresponding one of the lumens 16. Furthermore, the control handle 6 includes a stapling actuator 28 for operating the tissue stapling apparatus 12, a cover actuator 30 for operating the distal cover 20 and a cutting actuator 32 for operating the tissue cutting mechanism 14. As would be understood by those of skill in the art, the actuator 28 may be coupled to the tissue stapling apparatus 12 via, for example, a flexible, substantially torsionally stiff drive shaft (not shown) extending from the control handle 6, through the sheath 4 to the working head assembly 8.

As seen in FIG. 3, the distal openings 16a are preferably radially spaced around an entire circumference of the annular tissue receiving space 10 so that each of the grasping devices 18 exiting therefrom may draw a corresponding portion of the tissue of an organ within which the device is positioned into the tissue receiving space so that an entire circumference of the organ is drawn into the tissue receiving space 10 as will be described more fully below.

The grasping devices 18 for use with the device 2 may be formed as standard graspers with, for example, ratchet mechanisms (not shown) at proximal ends thereof allowing an operator to lock the grasping devices 18 in the closed position once a desired portion of tissue has been clamped therein. Furthermore, those skilled in the art will understand that other known tissue grabbing means may be employed such as, for example, T-Rex graspers, tissue anchors, gastrointestinal biopsy forceps, cardiac biopsy forceps, and/or the application of suction to the desired tissue.

Furthermore, a clamping mechanism 34 provided in the working head assembly 8 includes a plurality of clamping members 34a radially spaced from one another and positioned radially within the openings 16a. Thus, the tissue receiving space 10 extends between the radially outer surfaces of the clamping members 34a and an inner surface 36a of a housing 36 of the working head assembly 8. The clamping members 34a are preferably formed of a non-corroding material such as titanium or stainless steel and are pivotally coupled to the working head assembly 8 for movement between an open and a clamping position. As would be understood by those of skill in the art, any number of known mechanisms may be employed to actuate the clamping members 34a. An exemplary clamping mechanism shown in FIG. 7 includes a plurality of axially compressible, radially expandable members 38, each member 38 being located radially within a corresponding clamping member 34a. When in an axially extended position, each radially expandable member 38 is radially compressed so that the corresponding clamping member 34a is in an open position. A control cable (not shown) is coupled to the distal end of each radially expandable member 38 so that, when the control cable is drawn proximally from the device, the distal ends of each of the radially expandable members 38 axially compress and radially expand to drive the clamping members 34a into the clamping position.

Each of the clamps 34a is configured to provide between 15 and 50 pounds of force to the tissue when in the fully clamped position and more preferably provides approximately 40 pounds of force to the tissue clamped thereby. Those skilled in the art will recognize that the amount of force required depends on the number of staples to be fired and the amount of force required to fire each staple. Thus, when firing 10 staples with a 6 lb. force applied by each firing, each of the clamps may apply approximately 60 lbs. of clamping force to the tissue.

Figure 5:
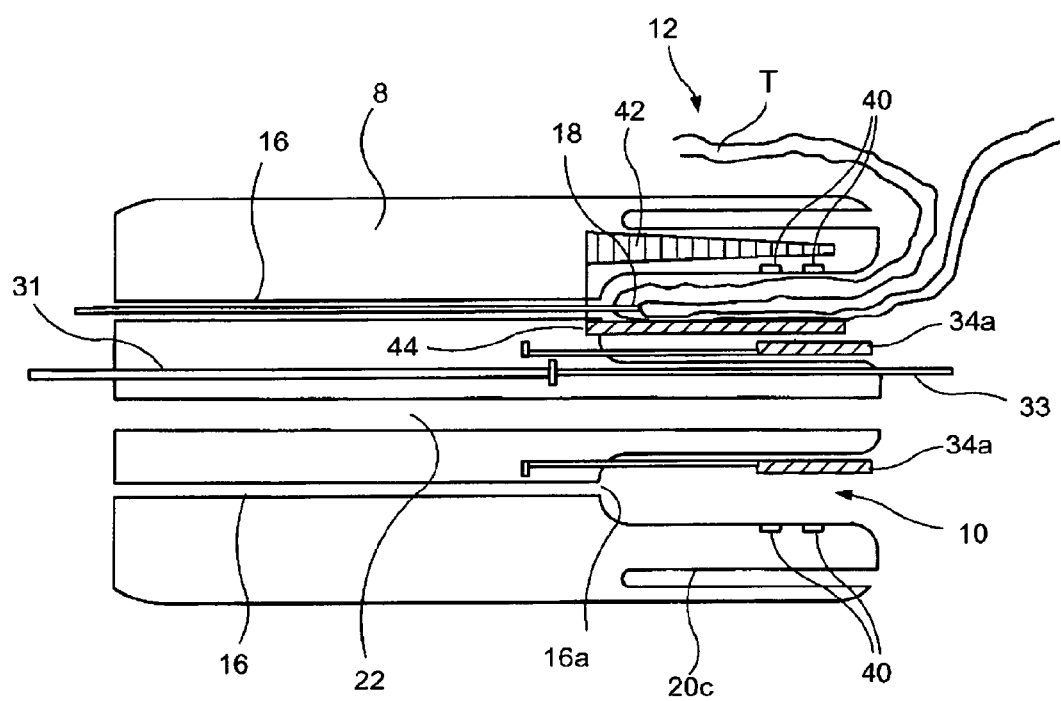
FIG. 5 shows a cross-sectional view of the working head assembly of the device of FIG. 1 with a tissue to be resected shown received in one portion thereof.

As shown in FIGS. 5 and 6, the stapling apparatus 12 includes a plurality of staple openings 40 formed in a predetermined pattern around a radially inward facing surface of the tissue receiving space 10 with a stapling mechanism 42 and an anvil member 44 rotating around the tissue receiving space to sequentially align with the staple openings 40 as the staple actuator 28 is operated by a user. The stapling mechanism 42 includes a staple cartridge 46 connected to a staple feed mechanism (not shown) as would be understood by those of skill in the art which positions staples in the staple openings 40. Once the staple feed mechanism has positioned a staple through a corresponding one of the staple openings 40, the staple actuator 28 drives a rotatable drive shaft (not shown) which moves the tapered anvil member 44 distally so that the progressively thicker proximal portions of the anvil member 44 come in contact with the legs of the staple bending it into the desired shape.

As shown in FIG. 5, the anvil member 44 according to this embodiment of the invention is formed as a rod extending radially inside the clamping members 34a. Alternatively, an anvil member 44 substantially mirroring the shape of the staple cartridge 46 may be employed so that, as the anvil member 44 is moved distally, the increasing width of the proximal portions of the anvil member 44 brings the staple into contact with the anvil member 44 and bends the staple into the desired shape. Furthermore, as would be understood by those of skill in the art, the anvil member 44 will be formed of sufficiently rigid material to absorb the force applied by the staples thereto without substantial deformation.

Alternatively, as shown in FIGS. 7 and 8, a stapling mechanism 42' may be formed as an annular cartridge 52 extending around a radially inner surface of the tissue receiving space 10 with the staple openings 40 facing radially outward into the tissue receiving space 10. A staple may then be loaded into the cartridge 52 before use of the device with an annular staple driving plunger 54 being received therewithin. In an initial configuration, a distal end of the plunger 54 is located proximally of the proximal-most one of the staple openings 40. The thickness of a beveled distal portion 54' of the plunger 54 increases from a minimum at the distal end so that, as the plunger 54 is advanced distally within the cartridge 52, the tapered portion 54' applies a gradually increasing radially outwardly directed force to each of a plurality of staples extending radially within corresponding staple openings 40. Furthermore, those skilled in the art will understand that by forming the distal portion 54' as, for example, a helical curve, the staples may be driven sequentially reducing the amount of force which would need to be applied to the plunger to that amount required to drive the portion of the staples which are being driven at a given moment.

As described above, in this apparatus, the staples are driven radially outward from a longitudinal axis of the working head assembly 8. Those skilled in the art will understand that the reaction force resulting from the stapling will be partially absorbed by the distal portion 54' of the plunger 54 as a hoop stress. Thus the distal portion 54' may be strengthened accordingly to absorb this stress without need to similarly strengthen the rest of the plunger 54.

Figure 9:
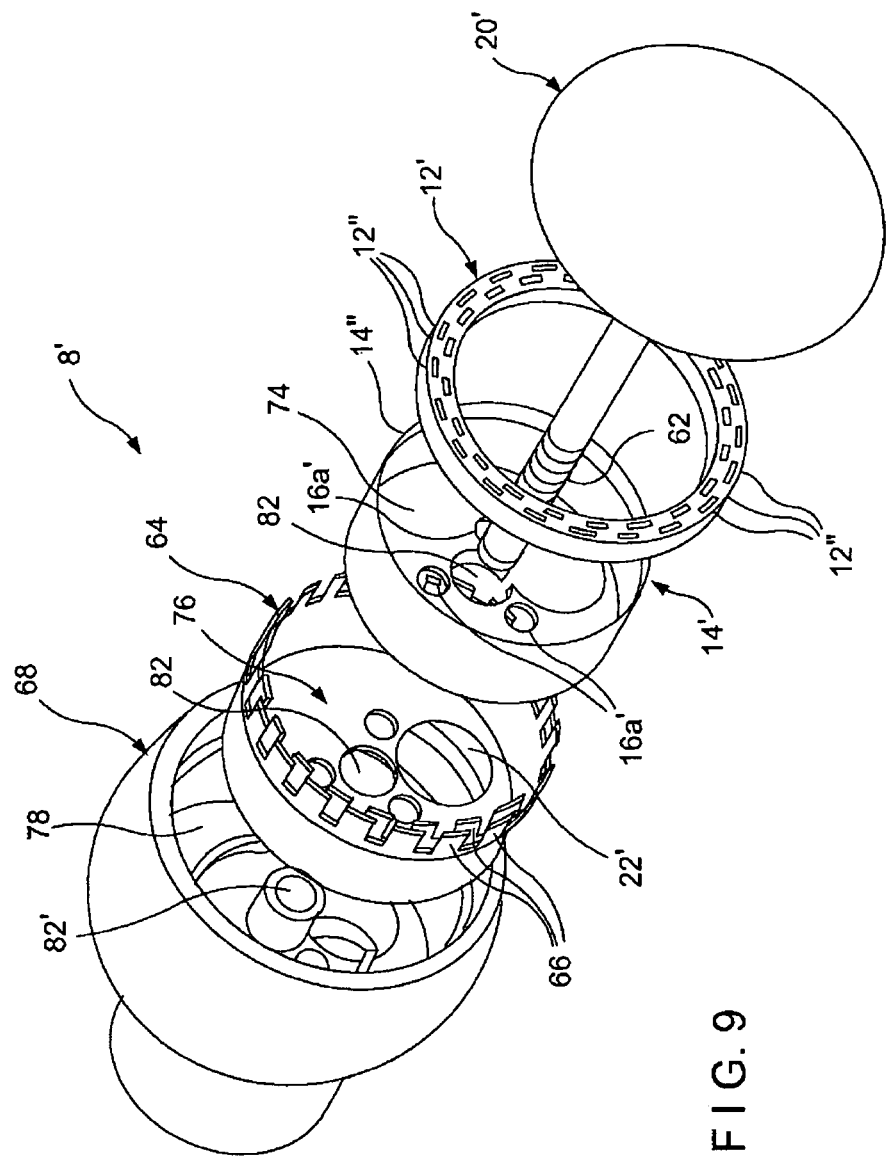
FIG. 9 shows an exploded view of a working head assembly according to a further embodiment of the invention.
Figure 10:
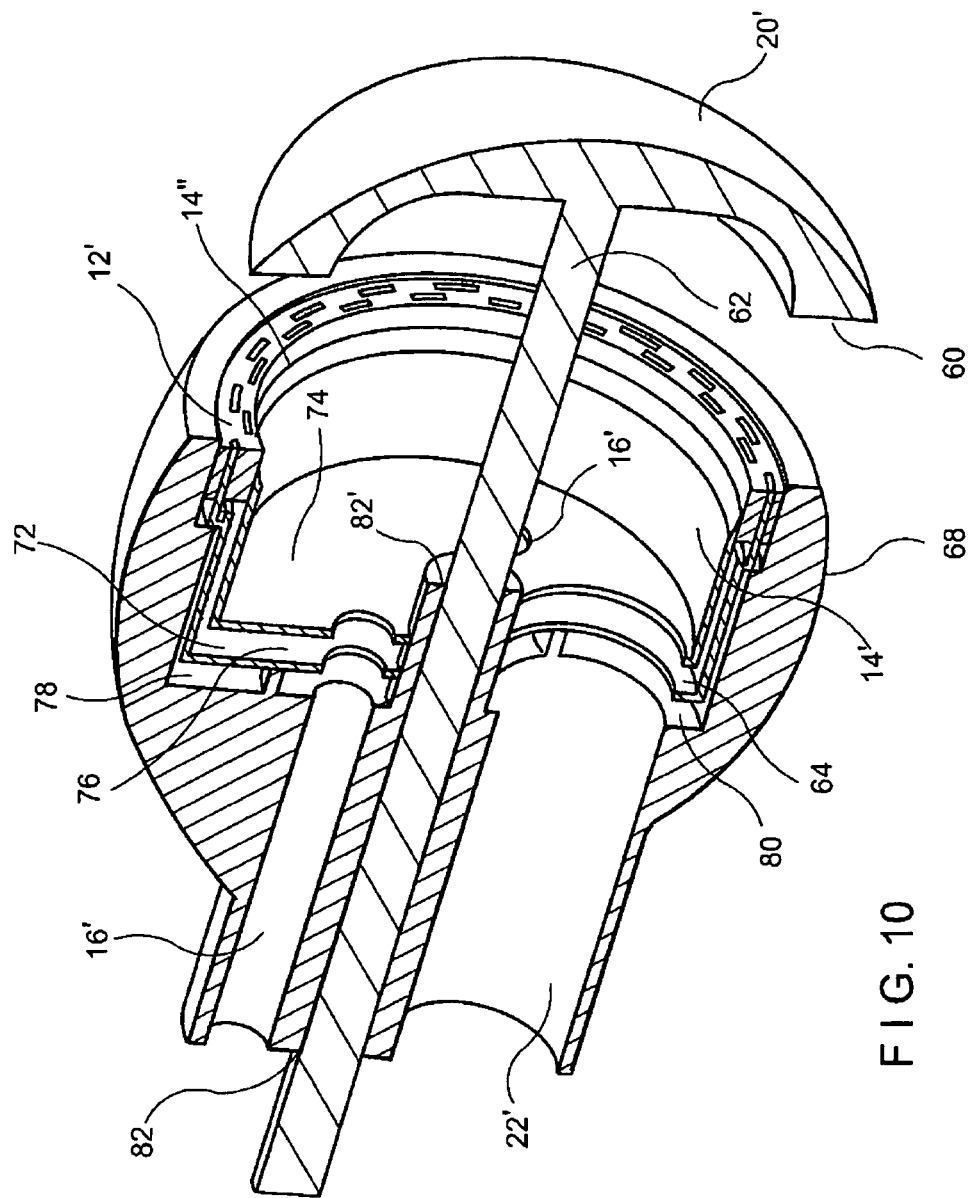
FIG. 10 shows a cross-sectional view of the working head assembly of FIG. 9.

FIGS. 9-13 show a working head assembly 8' according to a further embodiment of the invention. As shown in FIGS. 9 and 10, the working head assembly 8' includes a distal cover 20' including an anvil surface 60 formed on an annular proximally facing surface thereof. The anvil surface 60 faces a stapling apparatus 12' across a gap which varies in size depending on the relative positions of the distal cover 20' and the stapling apparatus 12' as will be described below. The stapling apparatus 12' includes a plurality of distally facing stapling openings 12'' which may be positioned so that they are aligned with a corresponding plurality of staple forming grooves in the anvil surface 60 as would be understood by those of skill in the art. The stapling apparatus 12' extends around an entire perimeter of a stapling area so that a full-thickness fold of an organ may be stapled around an entire circumference thereof. In the apparatus shown in FIGS. 9-13, this perimeter is substantially circular. However, those skilled in the art will understand that this shape may be adapted to any specific organ within which the anastomosis will take place. A tissue cutting mechanism 14' extends circumferentially within the stapling apparatus 12' so that tissue severed thereby will be radially within a line of staples placed by the stapling apparatus 12'. That is, when portions of a substantially tubular organ have previously been stapled to one another around an entire circumference thereof, the cutting mechanism 14' will be positioned to cut only that tissue which is between the line of staples and the fold of tissue so that no opening in the organ is created by the severing of this tissue.

The stapling apparatus 12' is formed as a substantially circular ring with a central opening that accommodates the tissue to be drawn thereinto as well as an endoscope and grasping mechanisms as described above in addition to a threaded shaft 62 which moveably couples the distal cover 20' to the proximal portion of the working head assembly 8'. In addition, the stapling apparatus 12' includes a staple driver ring 64 extending radially outside the tissue cutting mechanism 14' so that each of a plurality of staple driving spurs 66 thereof extends into a corresponding one of the staple openings 12''. As seen in FIGS. 9 and 10, each of the tissue cutting mechanism 14' and the staple driver ring 64 includes a plurality of openings allowing grasper lumens 16', an endoscope lumen 22' and a lumen for the threaded shaft 62 to pass therethrough. As discussed in regard to the previous embodiments, known graspers or other gripping elements could be inserted through the lumens 16' to grip tissue and draw the tissue into a tissue receiving space in the interior of the cutting mechanism 14'. In addition, each of these openings aligns with a corresponding opening in a proximal cap 68 of the working head assembly 8'. A proximal end of the proximal cap 68 couples to a flexible sheath (not shown) as described in regard to the previous embodiments.

As seen in FIG. 10, when assembled, the tissue cutting mechanism 14' rests circumferentially within the stapling apparatus 12' with a first gap 72 between a proximal wall 74 of the tissue cutting mechanism 14' and a proximal wall 76 of the staple driver ring 64. A second gap 78 is formed between the proximal wall 76 and a wall 80 of the proximal cap 68. As discussed above, openings are formed through each of the wall 80 and the proximal walls 74, 76 for each of the grasper lumens 16' as well as the endoscope lumen 22'. A lumen 82 for the threaded shaft 62 is formed by the proximal cap 68 with a distally projecting part 82' of the lumen 82 extending through corresponding openings in the walls 74, 76. The threaded shaft 62 is keyed to the lumen 82 so that it does not turn relative thereto. A captured nut (not shown) is threaded onto the shaft 62 so that turning the nut by means of a flexible drive shaft causes the distal cover 20' and the anvil surface 60 to move proximally or distally (depending on the direction of rotation of the captured nut) relative to the stapling apparatus 12'. As would be understood by those skilled in the art, this relative movement of the anvil surface 60 and the stapling apparatus 12' forms or closes a gap therebetween. This arrangement allows the shaft 62 to maintain alignment of the staple forming grooves on the anvil surface 60 relative to the staple openings 12'' in the stapling mechanism 12'.

Figure 11:
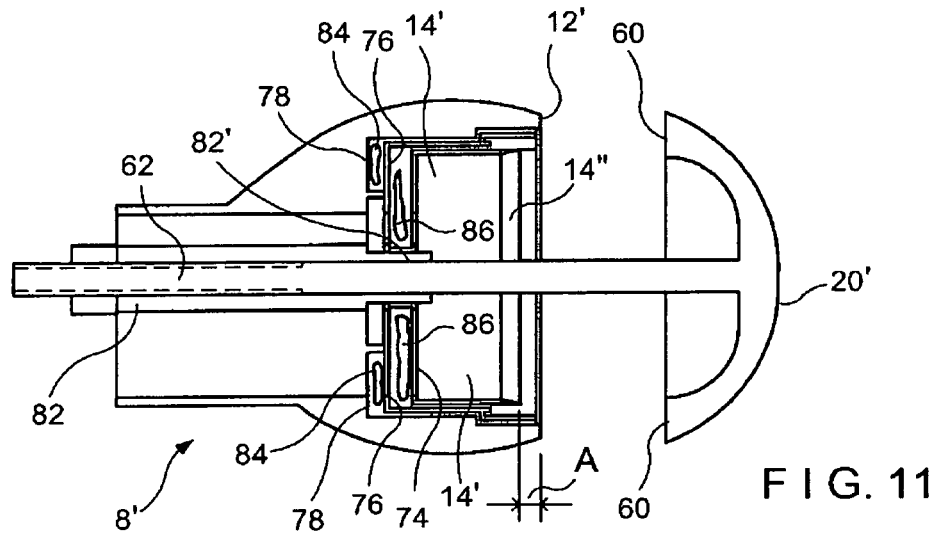
FIG. 11 shows a cross-sectional side view of the working head assembly of FIG. 9 with an anvil thereof in an extended tissue-receiving position.
Figure 12:
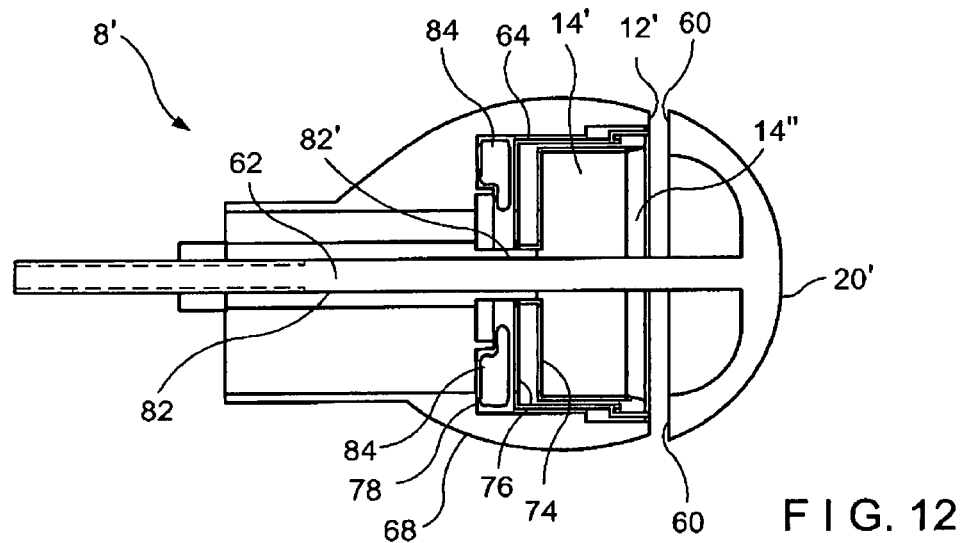
FIG. 12 shows a cross-sectional side view of the working head assembly of FIG. 9 with the anvil in a stapling position.
Figure 13:
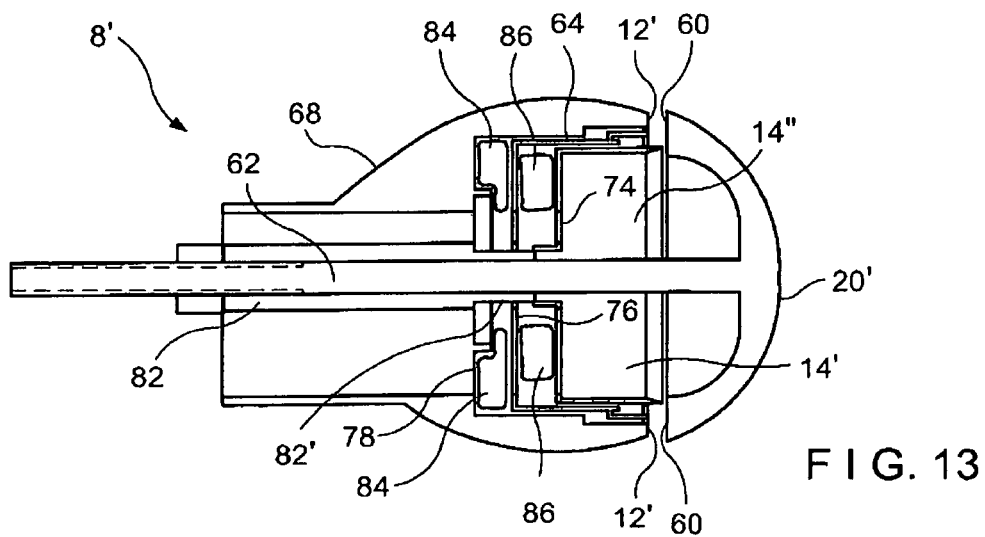
FIG. 13 shows a cross-sectional side view of the working head assembly of FIG. 9 with an anvil thereof in a cutting position.

As seen in FIGS. 11-13, a first balloon 84 coupled to a first inflation lumen (not shown) is positioned between the walls 76 and 78. The first balloon 84 may be substantially annular extending around an inner perimeter of the proximal cap 68. FIG. 11 shows a tissue grabbing configuration, when deflated, a distal tissue cutting surface 14'' of the tissue cutting mechanism 14' is recessed proximally of a distal surface of the stapling apparatus 12' by a distance A. As shown in FIG. 12, the first balloon 84 has been inflated driving both the staple driver ring 64 and the tissue cutting mechanism 14' distally by a distance substantially equal to A. This brings the distal tissue cutting surface 14'' flush with the distal surface of the stapling apparatus 12' and drives the staples across the gap between the anvil surface 60 and the staple openings 12''. The staples pass through the tissue grasped therebetween to couple the folds of tissue to one another around an entire perimeter of the organ. If the first balloon 84 extends around the entire perimeter of the proximal cap 68, the force applied to the wall 76 to drive the staple driver ring 64 and, consequently, to the tissue cutting mechanism 14' is distributed around the circumference thereof to aid in driving the staples from the staple openings 12'' around the entire circumference of the stapling apparatus 12'.

A second balloon 86 which extends between the walls 76 and 74, may also be annular to extend around an inner circumference of the staple driver ring 64. An inflation fluid is supplied to the second balloon 86 via a second inflation lumen (not shown) only after the first balloon 84 has been completely inflated to drive all of the staples through the tissue. Inflation of the second balloon 86 drives the tissue cutting mechanism 14' distally away from the staple driver ring 64 so that the cutting surface 14" slices through the tissue radially within the ring of stapled tissue to sever the tissue therefrom. The distal cover 20' is then moved distally to release the stapled tissue from between the anvil surface 60 and the stapling mechanism 12'. The distal cover 20' is then retracted proximally by rotating the captured nut on the threaded shaft 62 to expel the fluid from the first and second balloons 84, 86 and drive the tissue cutting mechanism back into the retracted position. This locks the severed tissue within the working head assembly 8' so that the severed tissue may be withdrawn from the body for analysis, etc.

Those skilled in the art will understand that, once the tissue radially within the ring of staples (i.e., closer to a central axis of the working head assembly 8') has been severed, the organ is maintained sealed by the ring of staples extending around an entire circumference thereof while a complete circumference portion of the organ has been removed. That is, a full circular anastomosis is performed completely endoluminally.

The above described embodiments are for purposes of illustration only and the various modifications of these embodiments which will be apparent are considered to be within the scope of the teachings of this invention which is to be limited only by the claims appended hereto.

What is claimed is:

1. A system for endoluminally performing an anastomosis of a substantially tubular organ, the system comprising:
   a flexible endoscope;
   an operative head slidably mountable on the endoscope, the operative head including a stapling mechanism and an anvil moveable relative to one another to define a tissue receiving space therebetween and a tissue cutting mechanism extending into the tissue receiving space proximal of the stapling mechanism, the stapling mechanism and the anvil being coupled to one another so that all components thereof remain within a lumen of the organ at all times during the anastomosis, the operative head further comprising:
      the tissue cutting mechanism formed as a substantially cylindrical element having a cylindrical side wall, a proximal end wall and a sharpened distal rim;
      a staple driver ring formed as a substantially cylindrical element, wherein the tissue cutting mechanism is configured to be movable independently of the staple driver ring; and
   a tissue gripping mechanism for drawing tissue from the organ into the tissue receiving space, wherein the portion of tissue drawn into the tissue receiving space extends around a complete circumference of the organ;
   wherein, operation of the stapling mechanism drives staples through a portion of tissue received within the tissue receiving space around the entire circumference thereof and, operation of the tissue cutting mechanism severs from the tissue through which the staples were driven a portion of tissue located within the tissue receiving space separated proximally therefrom.

2. The system according to claim 1, further comprising a control unit which remains outside a patient's body during use.

3. The system according to claim 2, wherein the control unit further includes a rotatable control member coupled to the stapling mechanism by a longitudinally flexible, torsionally stiff drive shaft.

4. The system according to claim 1, wherein the stapling mechanism rotates about a longitudinal axis of the operative head so that the stapling of the tissue is performed sequentially around a circumference thereof.

5. The system according to claim 4, wherein the anvil is coupled to the stapling mechanism and rotates therewith.

6. The system according to claim 1, wherein the tissue gripping mechanism includes a plurality of gripping jaws spaced from one another around a circumference of the tissue receiving space.

7. The system according to claim 1, wherein the tissue gripping mechanism includes a suction gripper.

8. An apparatus for performing endoluminal anastomosis of an organ, comprising:
   an operative head including an endoscope receiving lumen for slidably receiving a flexible endoscope therein, the operative head including a stapling mechanism and an anvil movable relative to one another to define a tissue receiving space therebetween, the stapling mechanism firing staples around an entire circumference of the tissue receiving space, the stapling mechanism and the anvil being coupled to one another so that all components thereof remain within a lumen of the organ at all times during the anastomosis, the operative head further including:
      a tissue cutting mechanism formed as a substantially cylindrical element having a cylindrical side wall, a proximal end wall and a sharpened distal rim;
      a lockout mechanism preventing the tissue cutting mechanism from operating until operation of the tissue stapling mechanism has been completed;
      a staple driver ring formed as a substantially cylindrical element wherein the tissue cutting mechanism is configured to be movable independently of the staple driver ring; and
   the tissue gripping mechanism for drawing into the tissue receiving space, a portion of tissue extending around an entire circumference of the organ.

9. The apparatus according to claim 8, further comprising a control handle which remains outside a patient's body while the apparatus is in use.

10. The apparatus according to claim 8, further comprising a flexible sheath extending between the operative head and the control handle and enclosing therein connections between the operative head and the control handle.

11. The apparatus according to claim 8, wherein the tissue gripping mechanism includes a plurality of graspers spaced from one another around the circumference of the tissue receiving space.

12. The apparatus according to claim 8, wherein the tissue cutting mechanism severs from the organ tissue received within the tissue receiving space.

13. The apparatus according to claim 8, wherein the operative head further includes a tissue clamping mechanism for holding the tissue within the tissue receiving space.

14. The apparatus according to claim 8, wherein the anvil is formed on a distal cap of the operative head, the distal cap being moveable between an insertion position in which the distal cap covers the tissue receiving space and an operative position in which the distal cap is withdrawn to expose the tissue receiving space.

* * * * *